United States Patent [19]

Konoshima

[11] 4,391,287
[45] Jul. 5, 1983

[54] CLEANING APPARATUS FOR ENDOSCOPE

[75] Inventor: Katunaga Konoshima, Hachioji, Japan

[73] Assignee: Olympus Optical Company Ltd., Japan

[21] Appl. No.: 240,951

[22] Filed: Mar. 5, 1981

[30] Foreign Application Priority Data

Apr. 11, 1980 [JP] Japan .................................. 55-47862

[51] Int. Cl.³ .............................................. B08B 3/12
[52] U.S. Cl. ........................................ 134/99; 134/93; 210/206
[58] Field of Search ....................... 210/206, 209, 751; 68/158; 134/99–101, 103, 93; 252/321

[56] References Cited

U.S. PATENT DOCUMENTS

| | | | |
|---|---|---|---|
| 2,632,736 | 3/1953 | Currie | 252/321 X |
| 2,993,223 | 8/1961 | Krammes | 252/321 X |
| 3,037,887 | 6/1962 | Brenner et al. | 134/101 X |
| 3,947,971 | 4/1976 | Bauer | 134/93 X |
| 4,064,885 | 12/1977 | Heckele | 134/95 |
| 4,281,674 | 8/1981 | Tanaka et al. | 134/95 |

Primary Examiner—Robert L. Bleutge
Attorney, Agent, or Firm—Ostrolenk, Faber, Gerb & Soffen

[57] ABSTRACT

A cleaning apparatus for endoscope is adapted to clean an endoscope with a cleaning liquid such as cleaning water, liquid detergent or the like. A liquid disinfectant circulating mechanism is provided which maintains a liquid disinfectant in circulation between a cleaning vessel and a tank of liquid disinfectant to disinfect the endoscope after the cleaning liquid has been drained. Apparatus is provided for supplying an antifoaming agent to the mechanism for effectively preventing a foaming from occurring in the presence of any residue of detergent.

11 Claims, 5 Drawing Figures

CLEANING APPARATUS FOR ENDOSCOPE

BACKGROUND OF THE INVENTION

The invention relates to a cleaning apparatus for an endoscope, and more particularly, to such cleaning apparatus including a cleaning vessel in which an endoscope which has been used is deposited and to which a cleaning water, a liquid detergent, a liquid disinfectant or the like is supplied to clean and disinfect the endoscope.

A cleaning apparatus of the kind described is available on the market, and usually comprises a mechanism for feeding a cleaning liquid such as cleaning water or liquid detergent to a cleaning vessel in which a used endoscope is deposited, and a liquid disinfectant circulating mechanism which feeds a liquid disinfectant to the cleaning vessel and circulates it between the vessel and a tank of liquid disinfectant after the cleaning liquid has been discharged from the cleaning vessel.

In the described cleaning apparatus, part of a drainage path for the cleaning liquid is also used as part of a circulating path for the liquid disinfectant, and the presence of any residue of a detergent component which remains after a water rinsing step to remove the liquid detergent used may cause the liquid disinfectant to foam during the subsequent disinfecting step. The amount of foam produced increases as the circulation of the liquid disinfectant is repeated until it eventually floods over the tank of liquid detergent or impedes the channel for the liquid disinfectant, which is a major disadvantage of the apparatus described.

SUMMARY OF THE INVENTION

It is an object of the invention to provide an endoscope cleaning apparatus which prevents foaming from being caused by any residue of liquid detergent even if a liquid disinfectant is circulated through a path which is common to both the liquid detergent and the liquid disinfectant.

In accordance with the invention, means for supplying an antifoaming agent is provided in a liquid disinfectant circulating mechanism so that the antifoaming agent is mixed with the liquid disinfectant. As a result, if channels for the liquid detergent and the liquid disinfectant are partly used in common a foaming within the disinfectant tank can be effectively prevented when the liquid disinfectant is set in circulation. Consequently, it is possible to eliminate completely the disadvantage of the prior art that the foam produced may flood over the disinfectant tank or impede the passage of the liquid disinfectant.

DESCRIPTION OF PREFERRED EMBODIMENTS

Figure 1:
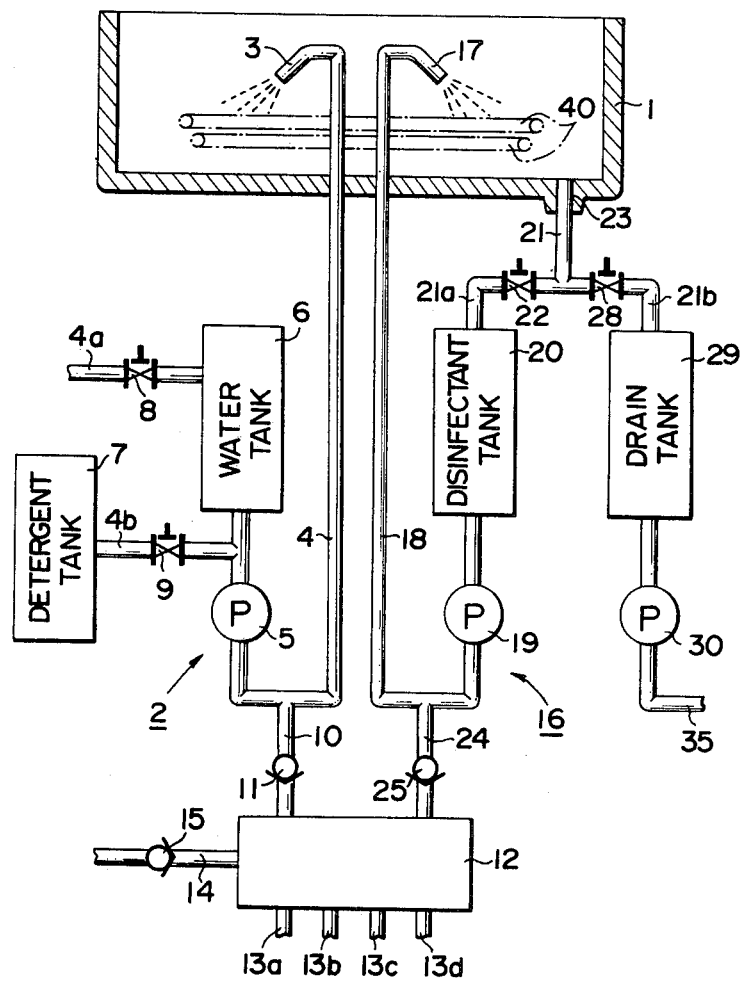
FIG. 1 is a schematic view of a cleaning apparatus for endoscopes to which the invention may be applied.

A cleaning apparatus for endoscopes to which the invention may be applied is generally arranged as shown in FIG. 1. Specifically, the cleaning apparatus comprises a cleaning vessel 1 in which a used endoscope 40 is disposed. A liquid detergent supply mechanism 2 includes a water tank 6, a tank of liquid detergent 7, a cleaning liquid feed pump 5, and a pair of solenoid valves 8, 9 which are operated to supply the water or liquid detergent. The mechanism 2 supplies a cleaning liquid to an injection head 3 which is disposed within the cleaning vessel 1. The apparatus also comprises a liquid disinfectant circulating mechanism 16 which includes a tank of liquid disinfectant 20, an associated feed pump 19, and a solenoid valve 22 which is operated to provide a reflux path for the liquid disinfectant. The mechanism 16 supplies the liquid disinfectant to another injection head 17 disposed within the cleaning vessel 1 and also causes a circulation of the liquid disinfectant between the cleaning vessel 1 and the tank 20 of liquid disinfectant. Additionally, the apparatus comprises a drain mechanism including a drain tank 29, a drainage pipe 30 and an associated solenoid valve 28 which form a drain path for draining the cleaning liquid supplied to the cleaning vessel 1 to the exterior, and an endoscope channel cleaning mechanism which includes a check valve 11 for supplying cleaning water, another check valve 25 for supplying liquid disinfectant, a check valve 15 for ventilation of the endoscope as with air, and a connector assembly 12 connected to the channels of the endoscope.

The water tank 6 is coupled to the faucet (not shown) of the water service through a conduit 4a, and the solenoid valve 8 is connected in the conduit between the tank 6 and the faucet. It is to be understood that the valve 8 is closed when a given level of cleaning water is reached in the tank 6, and is opened whenever the water level goes down, thus maintaining a given quantity of water in the tank 6. The water tank 6 is connected in communication with the injection head 3, disposed within the cleaning tank 1, through a supply tube 4 and the feed pump 5 connected therein. As the pump 5 is operated, the cleaning water from the tank 6 is supplied to the injection head 3. Another conduit 4b is connected across the tank 6 and pump 5, and is also connected to the tank 7 of liquid detergent through the solenoid valve 9. It will be understood that the valve 9 controls the supply of the liquid detergent from the tank 7.

The tank 20 of liquid disinfectant is connected to the injection head 17 disposed within the cleaning vessel 1 through a connection tube 18 and the feed pump 19 connected therein for spraying liquid disinfectant. As the pump 19 is operated, the liquid disinfectant is supplied from the tank 20 to the injection head 17. The tank 20 is also connected with a liquid disinfectant reflux tube 21a which is in turn connected through the reflux solenoid valve 22 to a drain tube 21 connected to a drain port 23 of the cleaning vessel 1.

The drain tank 29 is connected to the drain tube 21, which is in turn connected to the drain port 23 of the cleaning vessel 1, through another drain tube 21b and a drain solenoid valve 28. It will be appreciated that the drain tube 21 serves both as part of the circulating path of the liquid disinfectant and part of the drain path of the cleaning liquid. The end of the drain tube 21 remote from the drain port 23 is divided into two branches, one of which is connected to the reflux solenoid valve 22 while the other is connected to the drain solenoid valve 28.

A drainage tube 35 is connected to the drain tank 29 through the drainage pump 30, which when operated, serves to drain used cleaning liquid or the like externally from the tank 29.

A branch tube 10 which is connected to the tube 4 is connected to the connector assembly 12 through the check valve 11, which permits the cleaning water or liquid detergent as supplied from the tanks 6, 7 through the pump 5 to flow in only one direction, namely that is toward the connector assembly 12. A branch tube 24 which is connected to the connection tube 18 is also connected to the connector assembly 12 through the check valve 25, which permits the liquid disinfectant as supplied from the tank 20 through the pump 19 to flow in only one direction, that is, toward the connector assembly 12. Finally, the connector assembly 12 is connected through a ventilation tube 14 and ventilation check valve 15 connected therein to a ventilator (not shown). The check valve 15 allows the drying air supplied from the ventilator to flow toward the connector assembly 12.

The connector assembly 12 is provided with a plurality of connection tubes 13a to 13d which supply the cleaning water, liquid detergent, liquid disinfectant and drying air to forceps, ventilation, liquid feed and suction channels of the endoscope 40. It will be understood that the individual tubes 13a to 13d are connected to the opening of the respective channels which are defined in the body (not shown) of the endoscope 40. The branch tube 10 associated with the cleaning liquid, the branch tube 24 associated with the liquid disinfectant, the ventilation tube 14 and the connection tubes 13a to 13d communicate with each other through the connector assembly 12 so that the cleaning water, the liquid detergent, the liquid disinfectant and the air supplied from the tubes 10, 24, 14 are delivered to the respective channels in the endoscope through the connection tubes 13a to 13d.

Figure 2:
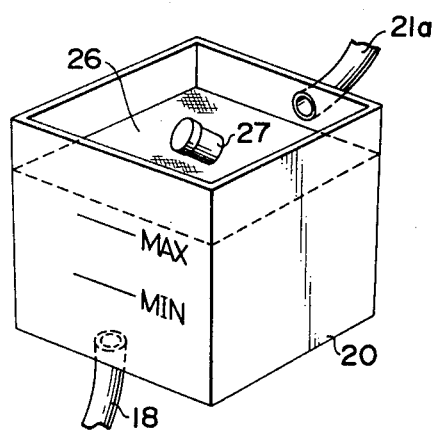
FIG. 2 is a perspective view of a tank of liquid disinfectant in a cleaning apparatus according to a first embodiment of the invention.

Referring to FIG. 2, the end opening of the reflux tube 21a associated with the liquid disinfectant is disposed above a mesh mechanism 26 which is fixedly mounted in the tank 20 and functioning as a strainer. In the present embodiment, a porous capsule 27 containing a quantity of antifoaming agent is placed on top of the mesh mechanism 26, and serves as means for supplying an antifoaming agent. The agent may comprise a silicone antifoaming agent, for example. The capsule 27 is formed with fine micropores so that the antifoaming agent may be dispersed and diffused into the liquid disinfectant in small increment for mixing therewith.

In operation, during a water rinsing step, the feed pump 5 is operated to supply the cleaning water from the tank 6 to the injection head 3, which then sprays it, thus water rinsing the endoscope 40. Simultaneously, the drain valve 28 is opened to provide a drainage. It is to be noted that the cleaning water is not only sprayed from the injection head 3, but is also fed to the ventilation and feed water channels within the endoscope through the connection tubes 13a to 13d, thus cleaning the interior of these channels.

The solenoid valve 9 associated with the liquid detergent is then opened to supply a liquid detergent such as a neutral detergent which is mixed into the cleaning water, thus performing a further cleaning operation by means of the detergent. Subsequently the valve 9 is closed and a water rinsing operation resumes. The pump 5 is then stopped, and after the liquid within the cleaning vessel 1 has been drained through the drain port 23, the valve 28 is closed while the reflux valve 22 is opened while pump 19 is energized. This permits the liquid disinfectant to be supplied from the tank 20 through the connection tube 18 to the injection head 17, which then sprays it, thus disinfecting the endoscope 40. After the disinfecting operation, the disinfectant cycles through the port 23, drain tube 21, valve 22, reflux tube 21a to be recovered by the tank 20 for re-use as a supply of liquid disinfectant for the feed pump 19. When the endoscope 40 has been disinfected by a circulation of the liquid disinfectant over a given time interval, the disinfectant is finally recovered by the tank 20. Subsequently, a water rinsing operation is commenced again to clean the endoscope 40 with water, thus completing a cleaning operation.

In the described cleaning apparatus, it will be noted that the liquid detergent finds its way through the cleaning vessel 1, drain port 23, drain tube 21, connector assembly 12 and connection tubes 13a to 13d, so that when the liquid disinfectant subsequently flows these paths during the disinfectant step, any residue of detergent which remains in the common path may be mixed into the liquid disinfectant. When a residue of the liquid detergent is mixed with the liquid disinfectant, it causes a foaming when the liquid disinfectant flows back into the tank 20 to be agitated therein. However, in the present embodiment, the tank 20 has the capsule 27 disposed therein which contains an antifoaming agent, which is thus mixed into the liquid disinfectant. This effectively prevents foaming from occurring within the tank 20. Accordingly, the difficulties of the foam produced possibly flooding over the tank 20 or possibly impeding the flow of the liquid disinfectant can be prevented. The use of the capsule for containing an antifoaming agent therein in the present embodiment facilitates its handling.

Figure 3:
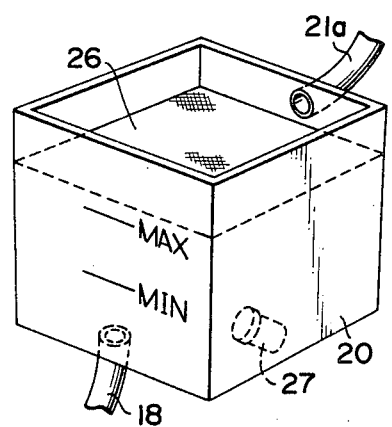
FIG. 3 is a perspective view of a tank of liquid disinfectant used in a cleaning apparatus according to a second embodiment of the invention.

It should be understood that the capsule 27 needs not be placed on top of the mesh mechanism 26 within the tank 20, but may be located in submerged position within the tank 20 as indicated by a second embodiment illustrated in FIG. 3, for example.

Figure 4:
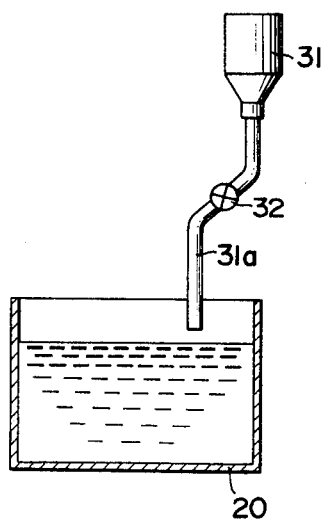
FIGS. 4 and 5 are schematic side elevations of means for supplying antifoaming agent in accordance with a third and a fourth embodiment of the invention.
Figure 5:
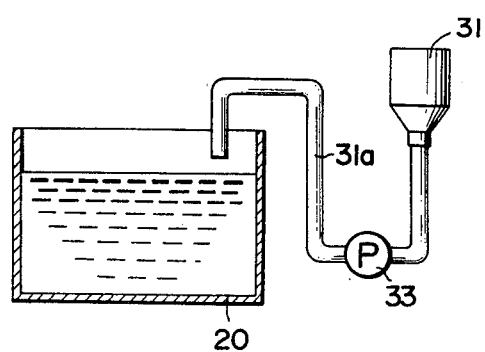

FIG. 4 shows a third embodiment in which a container 31 containing a quantity of antifoaming agent is located adjacent to the tank 20 of liquid disinfectant and coupled to the latter through a valve 32 connected in a supply tube 31a extending between the tank 20 and the container 31. By controlling the valve 32, the supply of the antifoaming agent from the container 31 can be controlled. FIG. 5 shows a fourth embodiment in which the antifoaming agent from the container 31 may be supplied into the tank 20 through a feed pump 33. It is to be understood that other various forms of means for supplying an antifoaming agent can be implemented, and the latter is not limited to specific embodiments disclosed herein.

What is claimed is:

1. A cleaning apparatus for an endoscope, comprising:
   a cleaning vessel; a cleaning liquid supply mechanism for supplying a cleaning liquid including liquid detergent or the like to the cleaning vessel in which an endoscope to be cleaned may be disposed;
   a drain pipe connected to the cleaning vessel and through which the cleaning liquid may be drained after it has been supplied to the cleaning vessel;

a liquid disinfectant circulating mechanism for supplying a liquid disinfectant including a tank for containing the disinfectant and being connected to the cleaning vessel to supply disinfectant to disinfect the endoscope after the cleaning liquid has been drained from the cleaning vessel, and the drain pipe being connectable to the tank for returning the liquid disinfectant from the cleaning vessel to the tank via the drain pipe, whereby residue detergent is mixed with the disinfectant as the disinfectant passes through the drain pipe; and means disposed within the liquid disinfectant circulating mechanism for supplying an anti-foaming agent therethrough which is effective to prevent a foaming from occurring in the presence of any residue of detergent which has mixed with the disinfectant.

2. A cleaning apparatus according to claim 1 in which the means for supplying antifoaming agent comprises a porous capsule containing a quantity of antifoaming agent, said capsule being disposed within the tank.

3. A cleaning apparatus according to claim 1 in which the means for supplying antifoaming agent includes a container containing a quantity of antifoaming agent, said container being disposed adjacent to the tank, an antifoaming agent in the container being supplied to the interior of the tank through a valve or a feed pump.

4. An endoscope cleaning apparatus, comprising:
(a) a cleaning vessel for receiving an endoscope which is to be cleaned;
(b) means for supplying a cleaning liquid having a detergent component to said vessel to clean said endoscope;
(c) a drain pipe connected to the cleaning vessel for draining from said cleaning vessel liquid that had been supplied to said cleaning vessel;
(d) means for supplying a liquid disinfectant through a circulation path extending from a supply tank containing said disinfectant to said vessel and back to said supply tank via said drain pipe to disinfect the endoscope after the cleaning liquid has been drained from said vessel, whereby residue detergent is mixed with said disinfectant as the disinfectant passes through said drain pipe; and
(e) means for supplying an anti-foaming agent to said circulation path.

5. The apparatus of claim 4, in which the means for supplying the antifoaming agent comprises a porous capsule containing a quantity of antifoaming agent; said capsule disposed in said circulation path.

6. The apparatus of claim 4, in which the means for supplying the antifoaming agent is a valve or feed pump connected in a supply path between a container containing a quantity of antifoaming agent and said circulation path.

7. The apparatus of claim 6, in which said circulation path comprises a tank for the liquid disinfectant and in which said antifoaming agent is supplied to said tank.

8. The apparatus of claim 4, in which said circulating path comprises a tank for the liquid disinfectant.

9. The apparatus of claim 8, in which said means for supplying the antifoaming agent comprises a porous capsule containing a quantity of antifoaming agent, said capsule disposed in said tank.

10. The apparatus of claim 9, in which said tank is configured with a mesh upon which said capsule is disposed.

11. The apparatus of any one of claims 4 through 10, in which said disinfectant liquid is circulated through a path which is common to both the cleaning liquid and the liquid disinfectant.

* * * * *